(12) United States Patent
Manginell et al.

(10) Patent No.: US 7,799,280 B1
(45) Date of Patent: *Sep. 21, 2010

(54) TORTUOUS PATH CHEMICAL PRECONCENTRATOR

(75) Inventors: Ronald P. Manginell, Albuquerque, NM (US); Patrick R. Lewis, Albuquerque, NM (US); Douglas R. Adkins, Albuquerque, NM (US); David R. Wheeler, Albuquerque, NM (US); Robert J. Simonson, Cedar Crest, NM (US)

(73) Assignee: Sandia Corporation, Albuquerque, NM (US)

( * ) Notice: Subject to any disclaimer, the term of this patent is extended or adjusted under 35 U.S.C. 154(b) by 1007 days.

This patent is subject to a terminal disclaimer.

(21) Appl. No.: 11/355,480

(22) Filed: Feb. 16, 2006

(51) Int. Cl.
*B01L 99/00* (2010.01)
(52) U.S. Cl. .................. 422/101; 422/99; 422/100; 210/510.1; 96/108; 96/143; 436/180
(58) Field of Classification Search .......... 422/99–101; 96/108, 143; 210/510.1; 436/180
See application file for complete search history.

(56) References Cited

U.S. PATENT DOCUMENTS

| | | | |
|---|---|---|---|
| 4,912,051 A * | 3/1990 | Zaromb | 436/178 |
| 6,171,378 B1 | 1/2001 | Manginell et al. | |
| 7,118,712 B1 * | 10/2006 | Manginell et al. | 422/101 |

2006/0130327 A1 * 6/2006 Pettit et al. .................. 29/890

OTHER PUBLICATIONS

N. K. Raman, "Template-Based approaches to the Preparation of Amorphous, Nanoporous Silicas," Chem, Mater., vol. 8, No. 8, 1996, 1682-1701.
M. P. Siegal, "Nanoporous-carbon films for microsensor preconcentrators," Applied Physics Letters, vol. 80, No. 21, May 27, 2002, 3940-3942.
R. P. Manginell, "Recent Advancements in the Gas-Phase MicroChemLab™," Proc. Of SPIE, vol. 5591, 44-55.
U.S. Appl. No. 10/696,649 filed Oct. 28, 2003.

* cited by examiner

*Primary Examiner*—Jyoti Nagpaul
(74) *Attorney, Agent, or Firm*—Kevin W. Bieg (57) ABSTRACT

A non-planar, tortuous path chemical preconcentrator has a high internal surface area having a heatable sorptive coating that can be used to selectively collect and concentrate one or more chemical species of interest from a fluid stream that can be rapidly released as a concentrated plug into an analytical or microanalytical chain for separation and detection. The non-planar chemical preconcentrator comprises a sorptive support structure having a tortuous flow path. The tortuosity provides repeated twists, turns, and bends to the flow, thereby increasing the interfacial contact between sample fluid stream and the sorptive material. The tortuous path also provides more opportunities for desorption and readsorption of volatile species. Further, the thermal efficiency of the tortuous path chemical preconcentrator is comparable or superior to the prior non-planar chemical preconcentrator. Finally, the tortuosity can be varied in different directions to optimize flow rates during the adsorption and desorption phases of operation of the preconcentrator.

12 Claims, 6 Drawing Sheets

FIG. 2B   Section A - A sample fluid          preconcentrated analyte

FIG. 2C   Section B - B

TORTUOUS PATH CHEMICAL PRECONCENTRATOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

CROSS-REFERENCE TO RELATED APPLICATION

This application is related to U.S. patent application Ser. No. 10/696,649, filed Oct. 28, 2003, which is incorporated herein by reference.

FIELD OF THE INVENTION

The present invention relates to chemical analysis and, more particularly, to a non-planar, tortuous path chemical preconcentrator with a high internal surface area having a heatable sorptive coating that can be used to selectively collect and concentrate one or more chemical species of interest from a fluid stream that can be rapidly released as a concentrated plug into an analytical or microanalytical chain for separation and detection.

BACKGROUND OF THE INVENTION

Portable, handheld microanalytical systems, which have been termed "chemical laboratories on a chip," are being developed to enable the rapid and sensitive detection of particular chemicals, including pollutants, high explosives, and chemical and biological warfare agents. Microfabricated analytical systems have the advantages of reduced power consumption and the ability to batch fabricate and assemble complete microanalytical systems on an integrated chip. In particular, increasing integration can reduce the lower limit of detectability by reducing dead volume and allowing for extremely short, heated transfer lengths between system components.

Current gas-phase microanalytical systems typically comprise a gas chromatography column to separate the chemical species, or analyte, in a gas mixture, and a detector to detect the separated species. Such microanalytical systems can also include a chemical preconcentrator. The chemical preconcentrator serves the important function of selectively collecting and concentrating the analyte(s) of interest out of a large gas sample volume on a sorptive material at the inlet of the microanalytical system. In particular, selective analyte preconcentration is an essential step for early-warning, trace chemical detection in real-world, high-consequence environments where a high background of potentially interfering compounds exists. The chemical preconcentrator can deliver an extremely sharp analyte plug to the downstream gas chromatograph by taking advantage of the rapid, efficient heating of the sorbed analyte with a low-heat capacity, low-loss microheater. The very narrow temporal plug improves baseline separations, and therefore the signal-to-noise ratio and detectability of the particular chemical species of interest. Further, with a rapid enough release, there is a greatly reduced need for mechanical means of sample introduction, such as valving. See R. P. Manginell et al., "Recent Advancements in the Gas-Phase MicroChemLab," *Proc. of SPIE* 5591, 44 (2004).

Previous microfabricated chemical preconcentrators have used a heated planar membrane suspended from a substrate as the microheater, wherein the sorptive material is disposed as a layer on a surface of the membrane to sorb the analytes from a gas stream. See U.S. Pat. No. 6,171,378 to Manginell et al., which is incorporated herein by reference. The high thermal efficiency, extremely low heat capacity, and low flow impedance of the planar preconcentrator enables very rapid thermal desorption of the chemical analyte with very low power consumption. In particular, the desorption rate is rapid enough to eliminate the need for a separate mechanical column injection loop. However, analyte uptake on the sorptive layer is low, due to sorptive materials limitations and the low collection area of the sorptive layer of the planar preconcentrator. In particular, the total collection capacity is inadequate for application to volatile compounds and materials, due largely to the low capacity of the planar adsorbent zone.

A non-planar chemical preconcentrator has also been developed that uses a high-surface area, low mass, three-dimensional, flow-through support structure that can be coated or packed with a sorptive material. See U.S. patent application Ser. No. 10/696,649 to Manginell et al., which is incorporated herein by reference. Two basic styles have been implemented. One employs flow perpendicular to the substrate surface, through a cylindrical adsorbent coating structure fabricated in the bulk of a silicon chip. The other allows the sample to flow parallel to the substrate surface through parallel, fin-like adsorbent coating structures. The high-surface area of the sorption support structure allows improved analyte collection and concentration, especially important for trace chemical detection. In particular, the measured collection capacity for semivolatile compounds on sol-gel adsorbents is increased by an order of magnitude, compared to the planar preconcentrator. Lithographically defined gas flow constrictions within the support structure improve mass transfer of analyte into and out of the adsorbent, so that while the transient electrothermal response of the non-planar preconcentrator can be two orders of magnitude longer than the planar preconcentrator, due to the added support mass, desorbed analyte peak widths are only a factor of two wider. However, while very successful, the low tortuosity of the flow through the support structure of the prior non-planar preconcentrator is not optimal for certain analytes. This low tortuosity can be alleviated by using a packed bed, which has a high capacity and nearly 100% capture efficiency for analyte collection. However, the packed bed has a very high flow impedance, requires relatively high power consumption, and has limited thermal transfer to the bed.

The non-planar chemical preconcentrator of the present invention comprises a sorptive support structure having a tortuous flow path. The tortuous path increases contact of the analyte with the sorptive material by reducing the boundary layer width, as compared with the prior non-planar preconcentrator support structure. It also provides more opportunities for desorption and readsorption of volatile species. Under certain flow conditions, vortices of flow can be created, further enhancing analyte collection and desorption. Therefore, the tortuous path preconcentrator provides a compromise between a planar preconcentrator and a packed bed preconcentrator. Further, the thermal efficiency of the tortuous path chemical preconcentrator is comparable or superior to the prior non-planar chemical preconcentrator. Finally, the tortuosity can be varied in different directions to optimize flow rates during the adsorption and desorption phases of operation of the preconcentrator.

SUMMARY OF THE INVENTION

The present invention is directed to a tortuous path chemical preconcentrator, comprising a substrate having a suspended membrane formed thereon; at least one resistive heating element disposed on a surface of the suspended membrane; a sorption support structure, comprising a structure having a tortuous flow path, disposed on a surface of the membrane; and a sorptive material disposed on the sorption support structure to sorb and concentrate at least one chemical species from a sample fluid, with the chemical species being releasable from the sorptive material upon heating of the sorptive material by the at least one resistive heating element.

The tortuosity provides repeated twists, turns, and bends to the flow, thereby increasing the interfacial contact between sample fluid stream and the sorptive material. For example, the sorption support structure comprises a plurality of baffles, crosses, diamond-like structures, dimpled structures, or splined structures. For example, the sorption support structure can comprise a herringbone or zigzag pattern. Further, the sorption support structure can have varying tortuosity in different directions. For example, the sorption support structure can have high tortuosity for enhanced collection in a loading direction and a relatively lower tortuosity to enhance desorption in an unloading direction.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIGS. 2A-2C show a schematic illustration of a tortuous path chemical preconcentrator comprising a plurality of baffles as the sorption support structure.

DETAILED DESCRIPTION OF THE INVENTION

Preferably, a chemical preconcentrator provides both efficient adsorption, thereby collecting as much of the analyte as possible in a short time, and efficient desorption, thereby providing a sharp peak of analyte flux to the microanalytical chain. The efficiency of collection and release of analytes depends on a variety of factors, including analyte concentration in the sample gas stream, sample and carrier gas flow rates, adsorption and desorption kinetics, temperature of operation, and duration of heating during the release step. These efficiencies also depend on the tortuosity of the sorption support structures. The tortuous path chemical preconcentrator of the present invention comprises a micromachined tortuous flow path to enhance the collection and release of analytes from a fluid stream. Although the overall flow rate can be controlled by external pumps, local flow rates within the tortuous path preconcentrator will also depend on the details of the sorption support structures.

Figure 1:
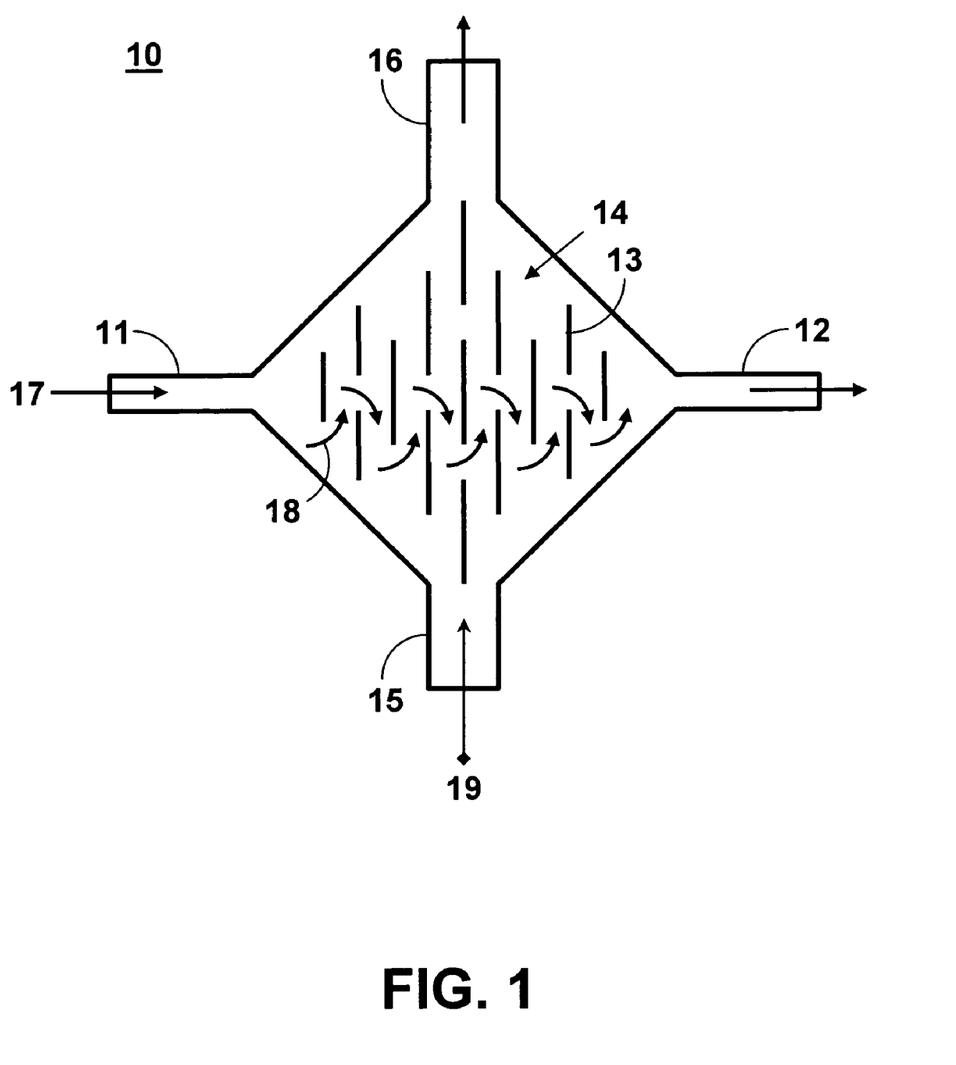
FIG. 1 shows a schematic illustration of a tortuous path chemical preconcentrator having varying tortuosity in two directions. Loading from left to right provides high tortuosity for enhanced collection. Unloading from the bottom has relatively lower tortuosity to enhance desorption.

In FIG. 1 is shown a schematic top-view illustration of an exemplary non-planar chemical preconcentrator 10 with varying tortuosity in two directions. The preconcentrator has a tortuous path sorption support structure 14 comprising a plurality of vertical (i.e., out of plane) baffles 13, a sample gas inlet 11, a sample gas outlet 12, a carrier gas inlet 15, and a carrier gas outlet 16. The vertical baffles 13 can be coated with a sorptive material to sorb analytes from the sample gas stream 17. The sample gas 17 enters the sample gas inlet 11 and the flow 18 is forced to follow a tortuous path to the right in and around the baffles 13 to the sample gas outlet 12. Therefore, tortuosity is provided by the baffles 13 having a structure transverse to the overall flow direction between the inlet 11 and the outlet 12. The tortuosity provides repeated twists, turns, and bends to the flow 17, thereby increasing the interfacial contact between sample fluid stream and the sorptive material. Therefore, loading of the analyte by flowing the sample gas 17 from left to right provides high tortuosity for enhanced collection. Conversely, unloading of the sorbed analytes by flowing the carrier gas 19 from the bottom to the top provides a relatively lower tortuosity to enhance desorption.

Figures 2A, 2B:
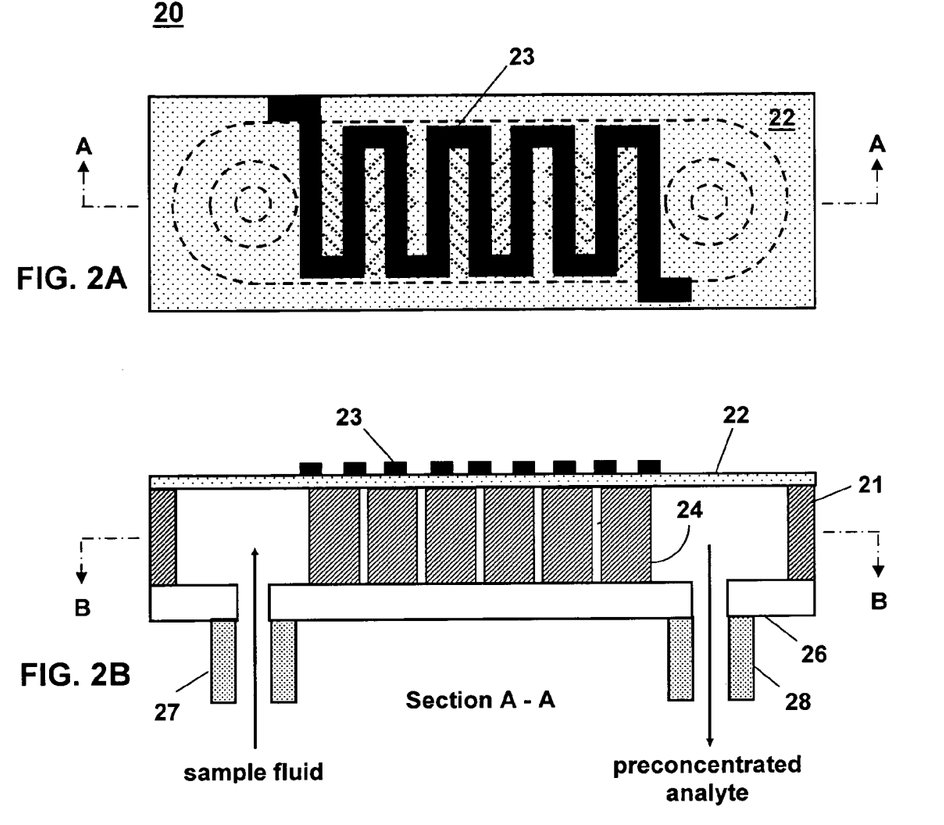
FIG. 2A shows a top view of the tortuous path chemical preconcentrator.
FIG. 2B shows a cross-sectional side view of the tortuous path chemical preconcentrator.
Figure 2C:
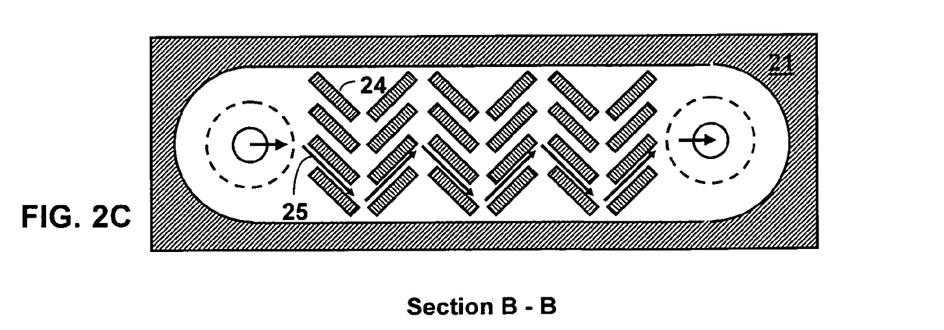
FIG. 2C shows a cross-sectional view of the tortuous path chemical preconcentrator.

In FIGS. 2A-2C is shown a schematic illustration of an embodiment of the tortuous path chemical preconcentrator 20, comprising a plurality of vertical baffles arranged in a herringbone pattern as the sorption support structure 24. The tortuous path chemical preconcentrator 20 can be fabricated using methods similar to those described by Manginell et al.

FIG. 2B shows a cross-sectional side view of the channel chemical preconcentrator 20, comprising a substrate 21, a membrane 22 suspended from the substrate 21, a resistive heating element 23 disposed on a surface of the suspended membrane 22, and the sorption support structure 24 comprising the plurality of vertical baffles disposed on the other surface of the membrane 22. The preconcentrator 20 can be fixtured with an attached glass lid 26 having an inlet capillary tube 27 for admitting a sample fluid and an outlet capillary tube 28 for providing a preconcentrated analyte containing the released chemical species of interest to the microanalytical chain. Alternatively, micro- or mesoscale manufacturing can be used to make other suitable fluidic connections to the preconcentrator.

The substrate 21 preferably comprises monocrystalline silicon, with a thickness of generally about 400-500 µm. However, other substrates can also be used, including other semiconductor materials (e.g., gallium arsenide), dielectric materials (e.g., a glass, crystalline quartz, fused silica, a plastic, or a ceramic), and metals (e.g., steel).

The membrane 22 is suspended and thermally isolated from the substrate 21. The membrane is typically formed as a rectangle (as shown) or square with lateral dimensions of about one to a few millimeters. The suspended membrane 22 is supported on its edges by attachment to the substrate 21. The suspended membrane 22 can be formed, for example, by depositing a film of the membrane material over a substrate and subsequently removing a portion of the substrate underlying the film. Similar to the prior chemical preconcentrators, low-pressure chemically vapor deposited (LPCVD) silicon nitride is a preferred membrane material due to its low stress, low thermal conductivity, and compatibility with integrated circuit (IC) processing steps. The membrane 22 is sufficiently thick (generally about 0.5-5 μm total thickness) for robustness as required for handling and to support the heating element 23 and the sorption support structure 24 and to withstand any thermally induced stresses. Other membrane materials can also be used, including silicon, polysilicon, plastics, etc.

In FIG. 2A is shown a top view of the tortuous path preconcentrator 20. The resistive heating element 23 can be a circuitous or serpentine metal trace on the membrane 22 that substantially covers the area of the sorption support structure 24 connected to the other side of the membrane 22. The resistive heating element 23 can comprise a resistive conducting material. The resistive heating element 13 can be formed by depositing one or more layers of a metal, metal alloy, or doped semiconductor over the membrane 22 on the opposite side from the sorption support structure 24 and patterning the layers to form the desired heater shape. Preferably, the resistive layer has a suitably high temperature of coefficient of resistance (TCR of 2500-3000 ppm/° C.) to facilitate temperature measurement and control. Alternatively, a separate temperature sensor (not shown) can be used to control and measure the temperature during heating of the sorption support structure 24.

In FIG. 2C is shown a cross-sectional view of the tortuous path preconcentrator 20. In this embodiment, the sorption support structure 24 comprises a plurality of baffles providing a herringbone pattern. The flow 25 is forced to follow a tortuous path through the herringbone pattern, thereby increasing the interfacial contact between sample fluid stream and the sorptive material. The baffles are preferably formed in the substrate 21 in a single masking and etching step. The height of the baffles can be controlled by the etching process.

As described by Manginell et al., the sorption support structure 24 can be formed on the membrane 22 by photolithography and backside etching of the substrate 21. The sorption support structure 24 can then be coated with a sorptive material. The sorptive material acts to sorb or concentrate one or more chemical species of interest from an ambient or fluid sample flowing through the structure over time and can rapidly release the chemical species in a concentrated plug upon rapid heating of the sorptive material using the resistive heating element. The sorptive material can comprise porous silicon, a sol-gel oxide, a polymer, a microporous material, or other adsorbent material. Specific adsorbent coating materials can be used to tailor analyte collection to specific applications. Besides selectivity, other desired coating properties include high adsorbency, high porosity for increased sorptive surface area, the ability to release the sorbed analyte thermally, and hydrophobicity so the coatings prevent water adsorption and signal degradation. The sorptive material can be applied by spray coating, traditional dip coating, solvent coating, vapor coating methods, or other coating methods.

For example, spray coating of a mesoporous sol-gel can be used to target semivolatile molecules. A sol-gel coating is a porous solid film formed from a liquid solution (sol) using a chemical reaction. The result is an adsorbent coating of a three-dimensional silica fossil determined by a template that has precise periodic porosity and extremely high surface area. See C. J. Brinker and G. W. Scherer, *Sol Gel Science: The Physics and Chemistry of Sol-Gel Processing*, Academic Press, San Diego, Calif. (1990). For example, the sol-gel known as A2 is selective for polar semivolatile molecules like chemical warfare agents, and it barely adsorbs volatile compounds like toluene or mixtures such as gasoline, jet fuel, and diesel. A thin film sol-gel coating A2 has a physical surface area over 1000 $m^2/g$, with a controlled pore size in the 1 to 5 nm range. A2** is made mesoporous by using the surfactant templating agent cetyl tetra ammonium bromide (CTAB). The template holds the pores open while the sol is gelling and crosslinking. After the devices are coated, they can be baked at 350° C. in nitrogen to remove the CTAB to preserve the hydrophobicity. See R. J. Kottenstette et al., "Improved Detection of Chemical Warfare Agents Using Functional Materials," American Chemical Society National Meeting, New York, N.Y., September 2003; and N. K. Raman et al., "Template-Based Approaches to the Preparation of Amorphous, Nanoporous Silicas," *Chemistry of Materials* 8(8), 1682 (1996).

For example, a pulsed-laser deposition of nanoporous-carbon coating can be used to target toxic industrial chemicals (TICs) and tri-halomethane (THM). Nanoporous-carbon is a purely graphitic form of carbon with negligible residual stress, which allows it to coat any surface to any desired thickness. Pulsed-laser deposition of this material allows for precise control of density, thickness, morphology, and porosity. The nanoporous-carbon can be grown at room-temperature in a controlled gas ambient with a focused 248 nm excimer pulsed-laser. Masking can be provided by a machined shadow mask. The resulting nanoporous coating is hydrophobic, and pore sizes are as small as 1 nm. See M. P. Siegal et al., "Nanoporous-carbon Films for Microsensor Preconcentrators," *Appl. Phys. Lett.* 80(21), 3940 (2002).

Figure 3A:
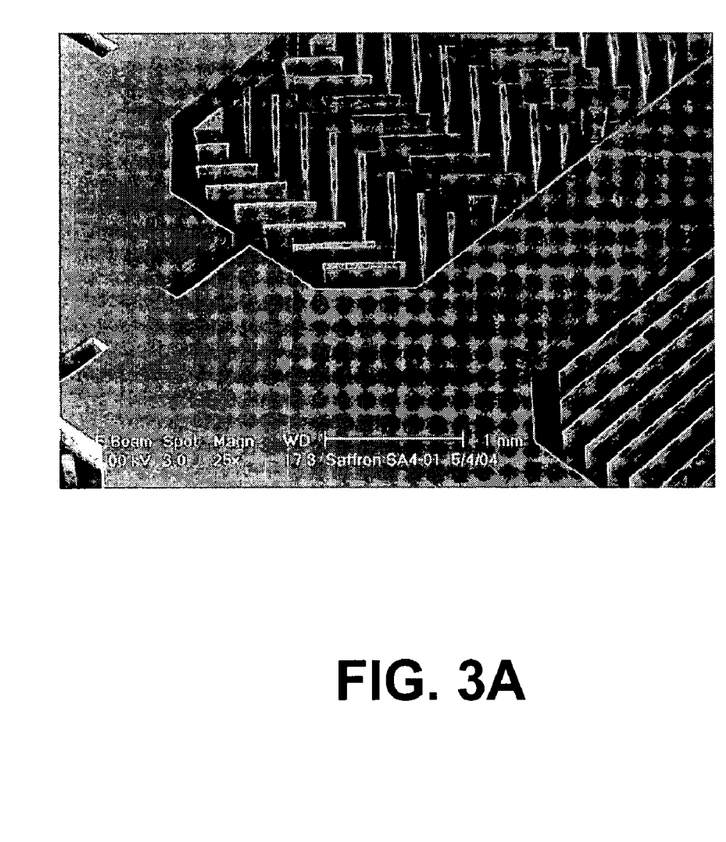
FIG. 3A shows a scanning electron micrograph (SEM) image of a tortuous path chemical preconcentrator wherein the sorptive support structure comprises herringbones or baffles.
Figure 3B:
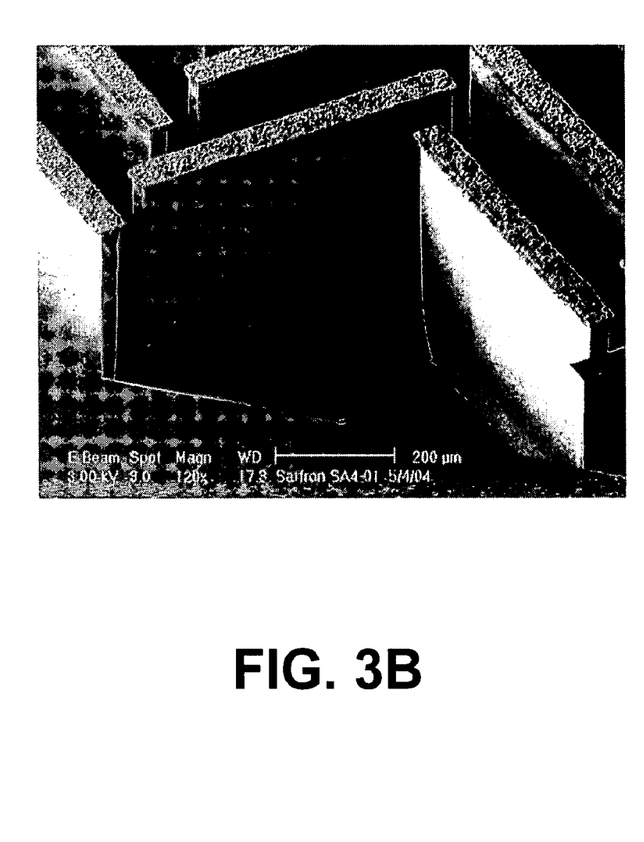
FIG. 3B shows a SEM of the sorptive support structure, showing the baffles interdigitated for increased tortuosity.

In FIG. 3A is shown a scanning electron micrograph (SEM) image of a tortuous path chemical preconcentrator wherein the sorptive support structure comprises vertical baffles in a herringbone pattern, as illustrated schematically in FIG. 2C. FIG. 3B shows a SEM of the sorptive support structure, showing the baffles interdigitated for increased tortuosity.

Figure 4A:
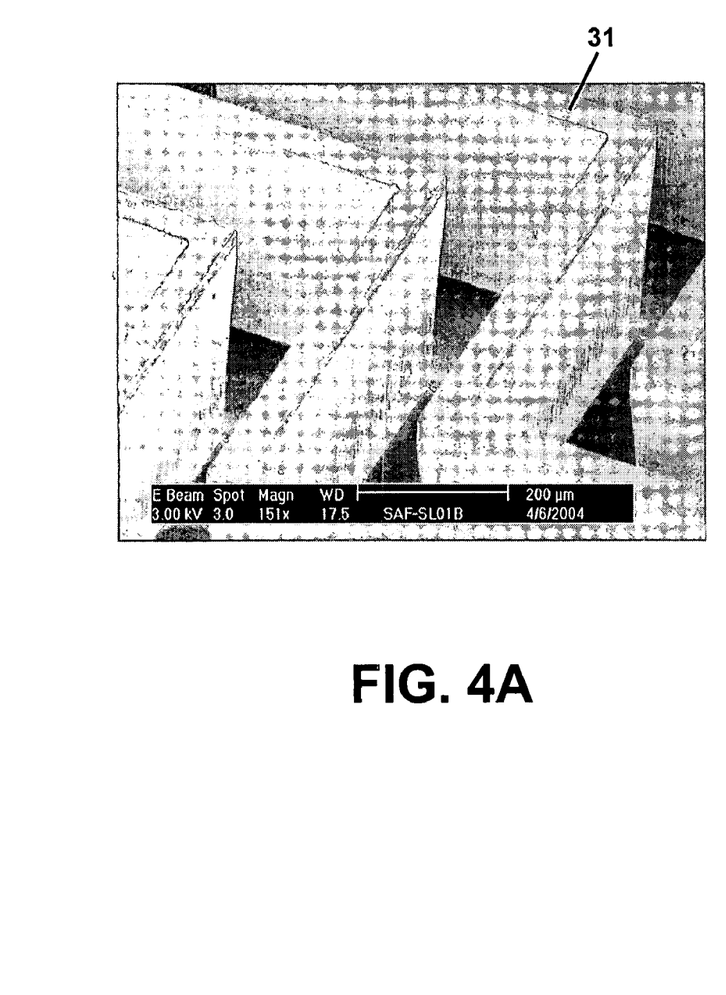
FIG. 4A shows a SEM of a tortuous path chemical preconcentrator with zigzag adsorbent coating walls.
Figure 4B:
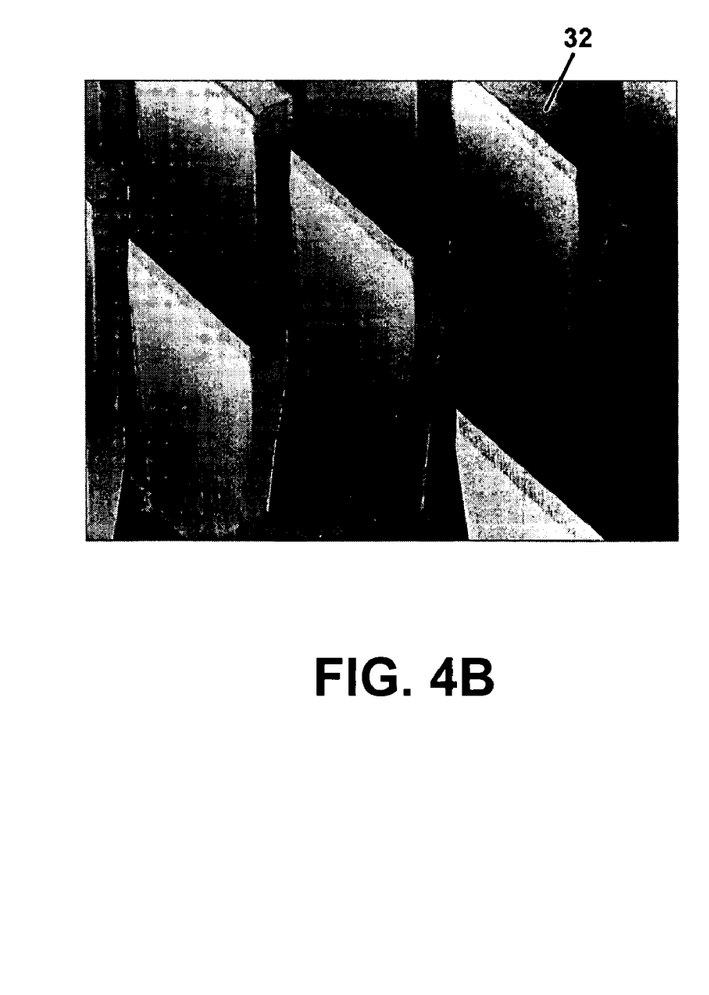
FIG. 4B shows a SEM of a tortuous path chemical preconcentrator with numerous rectangular baffles.
Figure 5:
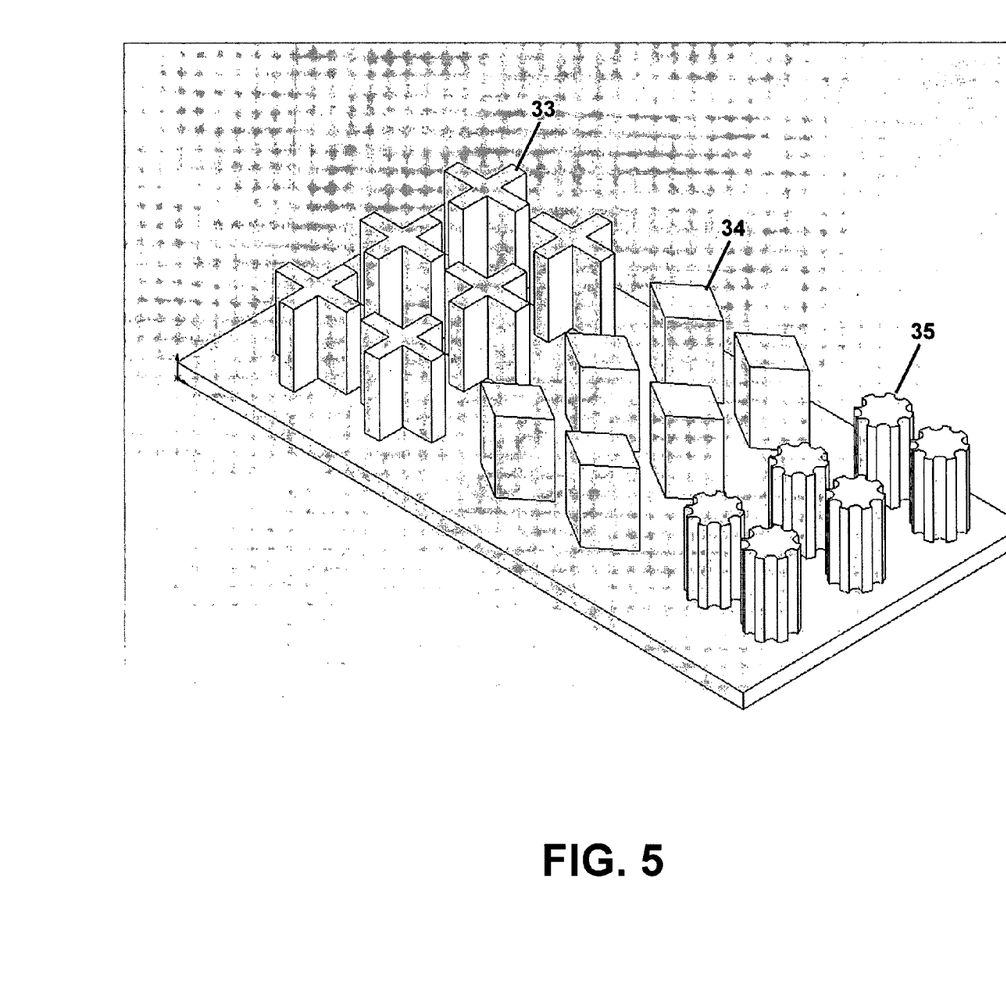
FIG. 5 shows examples of alternative sorption support structure geometries.

Alternative heater, sorptive coating, and sorption support structure configurations are possible. In FIG. 4A is shown a SEM of a tortuous path chemical preconcentrator with zigzag sorption support structure 31. In FIG. 4B is shown a SEM of a tortuous path chemical preconcentrator with numerous rectangular baffles 32 that can be configured perpendicular to the overall sample gas flow direction. In FIG. 5 are shown alternative sorption support structure geometries, including crosses 33, diamond-like structures 34, dimpled or splined structures 35, etc. It will be obvious to those skilled in the art that there are many other geometric structures that can add tortuosity and increased interfacial contact between sample fluid stream and the sorptive material.

Figure 6A:
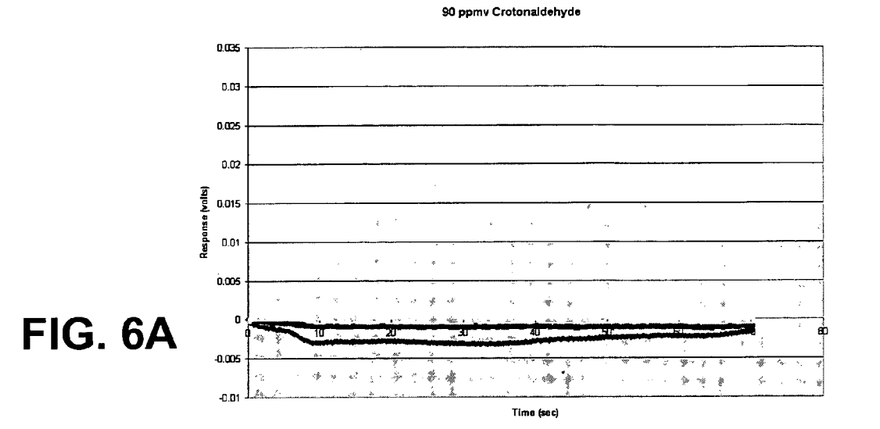
FIG. 6A shows the desorption profile for a planar preconcentrator for the collection of 90 ppmv Crotonaldhyde.
Figure 6B:
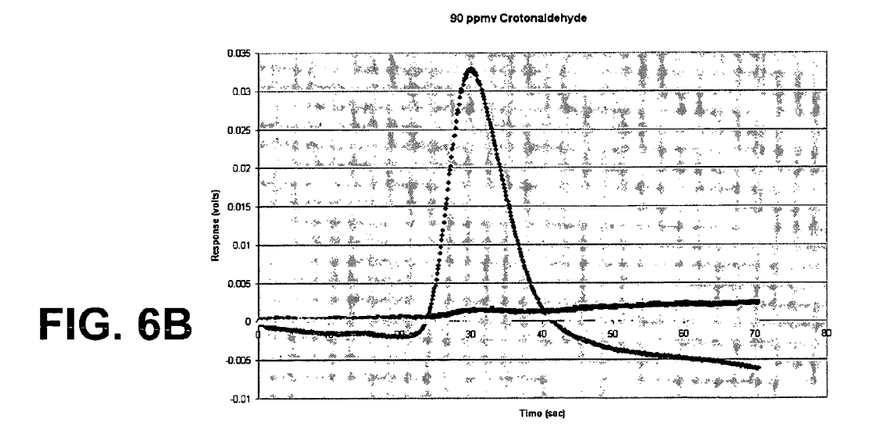
FIG. 6B shows the desoption profile for the tortuous path chemical preconcentrator for the same compound at the same concentration for the same collection time.

In FIGS. 6A and 6B are shown the performance of the tortuous path chemical preconcentrator relative to a prior planar chemical preconcentrator. Both preconcentrators had a sol-gel sorptive material and were pulse-heated to 200° C. during desorption. FIG. 6A shows the desorption profile for a planar preconcentrator resulting from a 60 sec collection of 90 ppmv of crotonaldehyde whose vapor pressure is 30 mmHg at 20° C. FIG. 6B shows the desorption profile for the tortuous path chemical preconcentrator for the same compound at the same concentration for the same collection time. A large desorption signal is observed at about 30 sec. for the tortuous path preconcentrator, whereas the planar preconcentrator showed essentially no response under the same conditions. A compound of the volatility of crotonaldehyde must have more than a single surface to sorb. When the breakthrough volume is small, another close-by sorbent surface is needed to reuptake the analyte. This is especially true for non-polar compounds.

Table 1 shows the collection efficiency for other high volatility compounds obtained using a tortuous path chemical preconcentrator (% efficiency=(area of injection peak)/(area of blow-by peak+area of injection peak)). Such high collection efficiencies have not been achieved with a planar preconcentrator.

TABLE 1

Collection Efficiencies for High Volatility Compounds Obtained Using a Tortuous Path Chemical Preconcentrator

| Analyte | Mass Injected (ng) | Area of Blow-by Peak | Area of Injection Peak | % efficiency | Vapor Pressure (mmHg @ 25 C.) |
|---|---|---|---|---|---|
| Methylene Chloride | 1657 | 2092 | 523 | 20 | 435 |
| Chloroform | 910 | 334 | 538 | 62 | 197 |
| Hexane | 613 | 926 | 3584 | 79 | 151 |
| Heptane | 236 | 11 | 1799 | 99 | 46 |

The present invention has been described as a tortuous path chemical preconcentrator. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A tortuous path chemical preconcentrator, comprising:
a substrate having a suspended membrane formed thereon;
at least one resistive heating element disposed on a surface of the suspended membrane;
a sorption support structure, comprising a structure having a tortuous flow path, disposed on a surface of the membrane; and
a sorptive material disposed on the sorption support structure to sorb and concentrate at least one chemical species from a sample fluid, with the chemical species being releasable from the sorptive material upon heating of the sorptive material by the at least one resistive heating element.

2. The tortuous path chemical preconcentrator of claim 1, wherein the sorption support structure comprises a material selected from the group consisting of dielectrics and semiconductors.

3. The tortuous path chemical preconcentrator of claim 2, wherein the sorption support structure comprises a material selected from the group consisting of silicon, polycrystalline silicon, silicon nitride, silicon oxynitride, and silicon carbide.

4. The tortuous path chemical preconcentrator of claim 1, wherein the sorption support structure comprises a plurality of baffles.

5. The tortuous path chemical preconcentrator of claim 1, wherein the sorption support structure comprises a herringbone pattern.

6. The tortuous path chemical preconcentrator of claim 1, wherein the sorption support structure comprises a zigzag pattern.

7. The tortuous path chemical preconcentrator of claim 1, wherein the sorption support structure comprises a cross, diamond-like structure, dimpled structure, or splined structure.

8. The tortuous path chemical preconcentrator of claim 1, wherein the suspended membrane is selected from the group consisting of semiconductors and dielectrics.

9. The tortuous path chemical preconcentrator of claim 8, wherein the suspended membrane comprises a material selected from the group consisting of silicon, polycrystalline silicon, silicon nitride, silicon oxide, silicon oxynitride, silicon carbide, and plastics.

10. The tortuous path chemical preconcentrator of claim 1, wherein the sorptive material comprises porous silicon, a sol-gel, oxide, polymer, or microporous material.

11. The tortuous path chemical preconcentrator of claim 1, wherein the sorption support structure has varying tortuosity in different directions.

12. The tortuous path chemical preconcentrator of claim 11, wherein sorption support structure has high tortuosity for enhanced collection in a loading direction and a relatively lower tortuosity to enhance desorption in an unloading direction.

* * * * *